(12) United States Patent
Khan et al.

(10) Patent No.: US 6,387,409 B1
(45) Date of Patent: May 14, 2002

(54) COMPOSITION AND METHOD OF PREPARING MICROPARTICLES OF WATER-INSOLUBLE SUBSTANCES

(75) Inventors: Sheema Khan, Napean (CA); Gary W. Pace, Durham, NC (US)

(73) Assignee: RTP Pharma Inc., Durham, NC (US)

( * ) Notice: Subject to any disclaimer, the term of this patent is extended or adjusted under 35 U.S.C. 154(b) by 0 days.

(21) Appl. No.: 09/477,351

(22) Filed: Jan. 4, 2000

Related U.S. Application Data

(62) Division of application No. 09/277,726, filed on Mar. 29, 1999, now abandoned.
(60) Provisional application No. 60/079,809, filed on Mar. 30, 1998.

(51) Int. Cl.$^7$ .................................................. A61K 9/14
(52) U.S. Cl. ....................................... 424/489; 424/401
(58) Field of Search ................................ 424/401, 489

(56) References Cited

U.S. PATENT DOCUMENTS

| | | |
|---|---|---|
| 5,091,187 A | 2/1992 | Haynes ........................ 424/450 |
| 5,145,684 A | 9/1992 | Liversidge et al. .......... 424/489 |
| 5,298,262 A | 3/1994 | Na et al. ..................... 424/489 |
| 5,326,552 A | 7/1994 | Na et al. ........................ 424/4 |
| 5,336,507 A | 8/1994 | Na et al. ..................... 424/489 |
| 5,340,564 A | 8/1994 | Illig et al. ....................... 424/9 |
| 5,470,583 A | 11/1995 | Na et al. ..................... 424/489 |
| 5,510,118 A | 4/1996 | Bosch et al. ................ 424/489 |
| 5,569,448 A | 10/1996 | Wong et al. ................ 424/9.45 |
| 5,851,275 A | 12/1998 | Amidon et al. ........... 106/148.1 |
| 5,858,410 A | 1/1999 | Muller et al. ................ 424/489 |
| 5,922,355 A * | 7/1999 | Parikh et al. ................ 424/489 |

FOREIGN PATENT DOCUMENTS

| | | |
|---|---|---|
| EP | 0 499 299 A2 | 8/1992 |
| EP | 0 580 690 B1 | 3/1996 |
| WO | WO 96/24332 | 8/1996 |
| WO | WO 97/14407 | 4/1997 |
| WO | WO 98/07414 | 2/1998 |
| WO | WO 99/29300 | 6/1999 |

OTHER PUBLICATIONS

La Fuma Polymery 1998 43 nr 2, 104–108 The role of water–soluble polymers at the solid/liquid etc.
Luckham Pestic. Sci., 1989, 25, 25–34 The Physical Stability of Suspension Concentrates with Particular etc.
Calvõr et al Pharm. Dev. Tech., 3(3), 297–305, 1998 Production of Microparticles by High Pressure etc.
Siekmann et al Pharm. Pharmacol Lett (1994) 3: 225–228Melt–homogenized solid lipid nanoparticles etc.
Lourenco et al Int. J. Pharm. 138 (1996), 1–12 Steric stabilization of nanoparticles: size and surface properties.
Napper Polymeric Stabilizations of Colloidal Dispersions 1983.
Müller et al Emulsions and Nanosuspensions Chapter 9 1998 p 163.

* cited by examiner

*Primary Examiner*—Jose' G. Dees
*Assistant Examiner*—Konata M. George
(74) *Attorney, Agent, or Firm*—Nixon & Vanderhye

(57) ABSTRACT

Compositions and procedures that yield sub-micron and micron-size stable particles of water-insoluble or poorly soluble drugs or other industrially useful insoluble compounds are prepared using combinations of natural or synthetic phospholipids, a charged surface modifier such as a highly purified charged phospholipid and a block copolymer coated or adhered onto the surfaces of the water insoluble-compound particles. The combination of charged surface modifier and block copolymer allows the formation and stabilization of the sub-micron and micron size compound particles—stabilized by the charged phospholipid to provide electrostatic stabilization and the block copolymer to provide steric stabilization—and therefore prevents these particles from particle growth, aggregation or flocculation.

2 Claims, No Drawings

COMPOSITION AND METHOD OF PREPARING MICROPARTICLES OF WATER-INSOLUBLE SUBSTANCES

This application is a division of application Ser. No. 09/277,726 filed Mar. 29, 1999, now abandoned.

This application claims benefit of provisional application Ser. No. 60/079,809 filed Mar. 30, 1998, the disclosure of which is hereby incorporated by reference.

This invention relates to compositions and procedures that yield sub-micron and micron-size stable particles of water-insoluble or poorly soluble drugs or other industrially useful insoluble compounds. The compositions of this invention include combinations of natural or synthetic phospholipids, a charged surface modifier such as a highly purified charged phospholipid and a block copolymer coated or adhered onto the surfaces of the water insoluble-compound particles. The combination of charged surface modifier and block copolymer allows the formation and stabilization of the sub-micron and micron size compound particles—stabilized by the charged phospholipid surface modifiers to provide electrostatic stabilization and the block copolymer to provide steric stabilization—and therefore prevent these particles from particle growth, aggregation or flocculation.

BACKGROUND OF THE INVENTION

There is a critical need in the pharmaceutical and other biological based industries to formulate water-insoluble or poorly soluble substances into formulations for oral, injectable, inhalation and ophthalmic routes of delivery. Water insoluble compounds are those having poor solubility in water, that is <5 mg/ml at physiological pH (6.5–7.4). Preferably their water solubility is <1 mg/ml, more preferably <0.1 mg/ml. It is desirable that the drug is stable in water as a dispersion; otherwise a lyophilized or spray-dried solid form may be desirable.

As used herein, "micro" refers to a particle having diameter of from nanometers to micrometers. Microparticles, as used herein, refer to solid particles of irregular, non-spherical or spherical shapes. Formulations containing these microparticles provide some specific advantages over the unformulated non-micronized drug particles, which include improved oral bioavailability of drugs that are poorly absorbed from GI tract, development of injectable formulations that are currently available only in oral dosage form, less toxic injectable formulations that are currently prepared with organic solvents, sustained release of intramuscular injectable drugs that are currently administered through daily injection or constant infusion, and preparation of inhaled, ophthalmic formulation of drugs that otherwise could not be formulated for nasal or ocular use.

Current technology for delivering insoluble drugs as described in U.S. Pat. Nos. 5,091,188; 5,091,187 and 4,725,442 focuses on (a) either coating small drug particles with natural or synthetic phospholipids or (b) dissolving the drug in a suitable lipophilic carrier and forming an emulsion stabilized with natural or semisynthetic phospholipids. One of the disadvantages of these formulations is that certain drug particles in suspension tend to grow over time because of the dissolution and reprecipitation phenomenon known as the "Oswald ripening" or particle growth, as the solvent becomes saturated with solute, the larger particles grow and become even larger, Luckham, Pestic. Sci., (1999) 25, 25–34.

Another approach, as described in a series of patents uses a cloud point modifier(s). In U.S. Pat. Nos. 5,298,262; 5,326,552; 5,336,507; 5,304,564 and 5,470,583 a poorly soluble drug or diagnostic agent has adsorbed on its surface both a cloud-point modifier and a non-crosslinked nonionic surfactant. The role of the cloud point modifier is to increase the cloud point of the surfactant such that the resulting nanoparticles are resistant to particle size growth upon heat sterilization at 121° C.

DESCRIPTION OF THE INVENTION

The present invention focuses on preparing submicron to micron size particles using a combination of electrostatic and steric stabilization using at least one charged surface modifier and at least one block copolymer, with particles coated with a natural phospholipid. In this manner the growth of particle size, and hence storage stability, is controlled by adding a combination of electrostatic and steric stabilizing materials.

The use of this particular combination of electrostatic and steric stabilizers in addition to a natural phospholipid is characterized by its ability to result in volume weighted mean particle size values that are smaller than what can be achieved using phospholipid alone without the use of a surfactant with the same energy input, and provide compositions resistant to particle size growth on storage. In order to achieve the advantages of the present invention it is necessary that the natural phospholipid and stabilizers all be present at the time of particle size reduction or precipitation.

Another aspect of the present invention includes free-flowing powders of poorly soluble or insoluble drug substances such as cyclosporin as well as solid dosage forms of these powders, for instance in the form of compressed tablets and the like. Surprisingly we have found that microparticle formulations exhibit enhanced stability as illustrated in the data that follows.

Although we do not wish to be bound by any particular theory, it appears that these surface modifiers generally, that is phospholipids and one or more surfactants, adsorb to the surfaces of drug particles, and (a) convert lipophilic to hydrophilic surfaces with increased steric hindrance/stability, and (b) possibly modify zeta potential of surfaces with more charge repulsion stabilization. The concentrations of surface modifiers used in the process described here are normally above their critical micelle concentrations (CMC) and hence facilitate the formation of sub-micron to micron particles by stabilizing the small particles as they are formed to prevent reaggregation.

Phospholipid and surface modifier(s) are adsorbed onto the surfaces of drug particles in sufficient quantity to retard drug particle growth, reduce drug average particle size from 5 to 100 $\mu$ to sub-micron and micron size particles by one or combination of methods known in the art, such as sonication, homogenization, milling, microfluidization, precipitation or recrystallization or precipitation from supercritical fluid, and maintain sub-micron and micron size particles on subsequent storage as suspension or solid dosage form.

The formulations prepared by this invention may be dried, e.g., by lyophilization, fluid or spray drying, into powders, which can be resuspended or filled into capsules or converted into granules or tablets with the addition of binders and other excipients known in the art of tablet making.

By industrially useful insoluble or poorly soluble compounds we include biologically useful compounds, imaging agents, pharmaceutically useful compounds and in particular drugs for human and veterinary medicine. Water insoluble compounds are those having a poor solubility in water, that is less than 5 mg/ml at a near neutral pH of 5 to 8, although the water solubility may be less than 1 mg/ml and even less than 0.1 mg/ml.

Examples of some preferred water-insoluble drugs include immunosuppressive agents such as cyclosporins including cyclosporine (cyclosporin A), immunoactive agents, antiviral and antifungal agents, antineoplastic agents, analgesic and anti-inflammatory agents, antibiotics, antiepileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, hormones, and nutrients. A detailed description of these and other suitable drugs may be found in *Remington's Pharmaceutical Sciences,* 18th edition, 1990, Mack Publishing Co. Philadelphia, Pa.

The phospholipid may be any naturally occurring phospholipid or mixtures of phospholipids, sometimes referred to herein as "commercial" phospholipids, such as egg or soybean phospholipid or a combination thereof. The phospholipid may be salted or desalted, hydrogenated or partially hydrogenated or natural semisynthetic or synthetic. Examples of commercially available phospholipids include but are not limited to egg phospholipids P123 (Pfanstiehl), Lipoid E80 (Lipoid); and hydrogenated soy phospholipids Phospholipon 90H and 100H (Natterman) and 99% pure egg and soy phosphatidyl choline (Avanti Polar Lipids). The amount of phospholipid present in the composition ranges from 0.01% to 50%, preferably from 0.05% to 20%.

Block copolymers used in the invention display a brush-like interfacial conformation and possible steric stabilization to the particles. Suitable block copolymers include polaxomers, such as Pluronic™ F68, F108 and F127, which are block copolymers of ethylene oxide and propylene oxide available from BASF; and poloxamines, such as Tetronic™ 908 (T908, T707, T909, T1107 and T1307), which are tetrafunctional block copolymers derived from sequential addition of ethylene oxide and propylene oxide to ethylenediamine available from BASF. In a preferred aspect of the invention, when free-flowing formulations are desired, the block copolymer will itself be a powder. The amount of block copolymer is between 0.01% and 20%, preferably from 0.1% to 10%.

The charged surface modifier(s) used in the present invention are highly purified phospholipids either isolated from natural products or prepared synthetically. For example, commercially available phosphatidylcholine contains a small percentage of charged phosphatides such as phosphatidyl glycerol, phosphatidyl inosite, phosphatidyl serine and phosphatidic acid and its salts. Other charged phospholipids include palmitoyl-oleyl-phosphatidyl-glycerol (POPG) and dimiristoyl phosphatidylglycerol sodium salt (DMPG). Combinations of charged phospholipids may be used. These materials are present in relatively small amounts and serve to allow smaller particle formation and inhibit aggregation. The amount of charged phospholipids ranges from 0.01% to 5.0% and preferably from 0.05% to 1.0%.

It is thought that some of the functions of the combination of surface modifiers as it relates to this invention are (a) suppressing the process of Oswald Ripening and therefore maintaining the particle size, (b) increasing the storage stability, minimizing agglomeration and sedimentation, and decreasing the particle growth during lyophilization and reconstitution; (c) adhering or coating firmly onto the surfaces of water-insoluble drug particles and therefore modifying the interfaces between the particles and the liquid in the resulting formulations; (d) increasing the interface compatibility between water-insoluble drug particles and the liquid; and (e) possibly orienting preferentially themselves with the hydrophilic portion sticking into the aqueous solution and the lipophilic portion strongly adsorbed at the water-insoluble drug particle surfaces; and (f) preventing aggregation of the small particles back to larger particles as they are being formed using size reducing equipment or precipitation.

Considerable variations as to the identities and types of charged surface modifier and especially the block copolymer should be expected depending upon the drug or active a agent selected as the surface properties of these small particles are different. The most advantageous agents for the insoluble drug will be apparent following empirical tests to identify the system/combination resulting in the requisite particle size and particle size stability on storage over time.

Various procedures can be used to produce these stable sub-micron and micron size particles including mixing the insoluble substance with charged surface modifier and block copolymer followed by sonication, milling, homogenization, microfluidization; or precipitating from a solution of the substance using antisolvent and solvent precipitation in the presence of the phospholipid and surfactant(s). Mannitol and other disaccharides and other agents may be added to adjust the final formulation to isotonicity as well as acting as a stabilizing aid during drying.

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers ($\mu$m=$10^{-6}$ meters), nanometers (nm=$10^{-9}$ meters) or Angstrom units (=0.1 nm). Volumes are given in liters (L), milliliters (mL=$10^{-3}$ L) and microliters ($\mu$L=$10^{-6}$ L). Dilutions are by volume. All temperatures are reported in degrees Celsius. The compositions of the invention can comprise, consist essentially of or consist of the materials set forth and the process or method can comprise, consist essentially of or consist of the steps set forth with such materials.

The invention is further explained with reference to the following preferred embodiments. The following general procedure was used for the examples; exceptions are noted.

Preparation of Premix

Commercial phospholipid, mannitol, charged surface modifier and block copolymer were first mixed with water using a hand mixer. The drug was added afterwards to the mixture, and mixed for 10 min–30 min at room temperature. In the case of cyclosporine, the pH was adjusted to 7.5–8.0 using 1N NaOH, and the premix was cooled to 12° C. using an ice bath. The batch size for cyclosporin was 200 g for ursodiol 50 g and for fenofibrate 200 g.

Processing Conditions

The premix was processed at a constant temperature and pressure by using high-pressure instrumentation that subjects the formulation to shear cavitation, impact, and attrition, that is in either a microfluidizer or a homogenizer.

| Formulation Type | Processing Machine | Total Passes at Operating Pressure | Average Pressure (kPsi) | Average Temperature (C.) |
|---|---|---|---|---|
| Cyclosporine | Avestin C-50 homogenizer | 200 | 18 | 10 |
| Ursodiol | Avestin C-5 homogenizer | 100 | 18 | 13 |
| Fenofibrate | Microfluidizer M110H | 50 | 18 | 5 |

A "pass" is defined as one cycle of the formulation through the different elements of the processing machine. The "pass" or cycle for each machine is as follows:

Avestin C-50 and C-5: Formulation is placed in inlet reservoir then passes to the homogenization valve, next a heat exchanger then back to the inlet reservoir. It is the homogenization valve that subjects the formulation to the forces of shear, cavitation, impact and attrition.

M110H: The formulation is first put through 20 passes of the bypass loop defined as follows: inlet reservoir to auxiliary processing module to heat exchanger then back to inlet reservoir. The resulting formulation is then put through the interaction chamber loop, defined as follows: inlet reservoir to auxiliary processing module to interaction chamber to heat exchanger then back to inlet reservoir, it is in the interaction chamber where the formulation is subject to the forces of shear, cavitation, impact and attrition. Following processing, each formulation was collected and placed in vials for stability testing. "MP" indicates microparticles falling within the range of 0.05 to 10 microns.

The five different types of stability tests are described as follows:

| Stability Test | Description |
|---|---|
| 4C | Sample stored at 4° C. (temperature controlled) |
| 25C | Sample stored at 25° C. (temperature controlled. 60% relative humidity) |
| 25C(2) | Sample stored at ambient room temperature - cyclosporine only |
| 40C | Sample stored at 40° C. (temperature controlled) |
| Shaking | Sample laid down on its side on a shaking table at ambient room temperature. The shaking speed was at 100 rpm–110 rpm. |
| Thermal Cycling | One cycle defined as follows: sample stored at 4° C. for 2–4 days, then at 40° C. for 2–4 days. |

EXAMPLE 1

Effect of steric and charged surface modifiers on particle size reduction. These experiments show that in the presence of phospholipid a combination effect of steric and charged stabilizers gives a smaller terminal particle size, than by, using either alone. In all cases, the total weight percent of surface modifiers (commercial phospholipid, block copolymer, charged surface modifier) is kept constant.

TABLE 1.1

MP Cyclosporine data (5% w/w micronized cyclosporine, 5.5% Mannitol) 200 g batches, processed on homogenizer Avestin C-50

| Sample | w/w % Lipoid E80 | w/w % DMPG | w/w % Pluronic F68 | # passes | Particle size (microns) |
|---|---|---|---|---|---|
| 1 | 10 | 0 | 0 | 209 | 2.62 |
| 2 | 9.5 | 0.5 | 0 | 217 | 1.20 |

TABLE 1.1-continued

MP Cyclosporine data (5% w/w micronized cyclosporine, 5.5% Mannitol) 200 g batches, processed on homogenizer Avestin C-50

| Sample | w/w % Lipoid E80 | w/w % DMPG | w/w % Pluronic F68 | # passes | Particle size (microns) |
|---|---|---|---|---|---|
| 3 | 9.0 | 0 | 1.0 | 177 | 1.77 |
| 4 | 8.7 | 0.45 | 0.95 | 210 | 1.08 |

TABLE 1.2

MP Ursodiol data (10% w/w Ursodiol, 5.5% Mannitol) 50 g batches, processed on homogenizer Avestin C-5

| Sample | w/w % Lipoid E80 | w/w % DPPE | w/w % Tetronic 908 | # passes | Particle size (microns) |
|---|---|---|---|---|---|
| 1 | 2.4 | 0 | 0 | 127 | 1.36 |
| 2 | 1.6 | 0 | 0.8 | 107 | 1.15 |
| 3 | 2.0 | 0.4 | 0 | 106 | 1.34 |
| 4 | 1.41 | 0.28 | 0.72 | 102 | 1.06 |
| 5 | 0 | 0.4 | 2.0 | 104 | 1.37 |

TABLE 1.3

MP Fenofibrate data (10% w/w Fenofibrate, 5.5% Mannitol) 200 g batches, processed on Microfluidizer M110H

| Sample | w/w % Lipoid E80 | w/w % DMPG | w/w % Poloxamer 407 | # passes | Particle size (microns) |
|---|---|---|---|---|---|
| 1 | 4.0 | 0 | 0 | 70 | 0.95 |
| 2 | 3.0 | 0 | 1.0 | 70 | 0.86 |
| 3 | 3.6 | 0.4 | 0 | 70 | 0.85 |
| 4 | 2.77 | 0.31 | 0.92 | 70 | 0.82 |

The data for cyclosporine, ursodiol and fenofibrate show the particle size reduction is maximal in phospholipid coated microparticles in the presence of charged surface modifier and a block copolymer. EXAMPLE 2

Effect of the presence of steric and charged stabilizers on the rate of particle size reduction. As the formulation passes through the homogenizer, the average diameter of the formulated particles reduces in magnitude. An empirical relation has been found that relates the average diameter to the pass number:

$$\text{Average diameter} = K/(\text{pass number})^\alpha$$

The above equation can also be used to determine how many passes it takes for the average diameter to reduce to 1 micron: # of passes to reach 1 micron=$(K)^{1/\alpha}$. These data demonstrate that steric and charged stabilizers improve the rate of particle formation.

TABLE 2.1

MP Fenofibrate data (10% w/w Fenofibrate, 5.5% Mannitol) Rate of particle size reduction - 200 g batches on the Mircofluidizer M110H

| Sample | w/w % Lipoid E80 | w/w % DMPG | w/w % Poloxamer 407 | Calculated # passes for 1 micron* |
|---|---|---|---|---|
| 1 | 4.0 | 0 | 0 | 44 |
| 2 | 3.0 | 0 | 1.0 | 33 |

TABLE 2.1-continued

MP Fenofibrate data (10% w/w Fenofibrate, 5.5% Mannitol)
Rate of particle size reduction - 200 g batches on the Mircofluidizer M110H

| Sample | w/w % Lipoid E80 | w/w % DMPG | w/w % Poloxamer 407 | Calculated # passes for 1 micron* |
|---|---|---|---|---|
| 3 | 3.6 | 0.4 | 0 | 37 |
| 4 | 2.77 | 0.31 | 0.92 | 27 |

*For Fenofibrate, the total pass number is the calculated value plus 20 passes of the formulation using the bypass loop.

TABLE 2.2

MP Ursodiol data (10% w/w Ursodiol, 5.5% Mannitol)
Rate of particle size reduction - 50 g batches on the Avestin C5 homogenizer

| Sample | w/w % Lipoid E80 | w/w % DPPE | w/w % Tetronic 908 | Calculated # passes for 1 micron |
|---|---|---|---|---|
| 1 | 2.4 | 0 | 0 | 305 |
| 2 | 1.6 | 0 | 0.8 | 158 |
| 3 | 2.0 | 0.4 | 0 | 261 |
| 4 | 1.41 | 0.28 | 0.72 | 134 |
| 5 | 0 | 0.4 | 2.0 | 230 |

The data for ursodiol and fenofibrate show the rate of particle size reduction is maximal in the production of phospholipid coated microparticles in the presence of charged surface modifier and a block copolymer.

EXAMPLE 3

Effect of steric and charged surface modifiers on particle stability. These data demonstrate the combination of charged phospholipid and block copolymer provide stability against Ostwald ripening and aggregation of the particles in the formulations.

TABLE 3.1

MP Cyclosporine data (5% w/w micronized cyclosporine, 5.5% Mannitol)
Particle size at room temperature

| Sample | w/w % Lipoid E80 | w/w % DMPG | w/w % Pluronic F68 | Initial size (microns) | Final size (microns) | Days |
|---|---|---|---|---|---|---|
| 1 | 10 | 0 | 0 | 2.62 | 8.07 | 66 |
| 2 | 9.5 | 0.5 | 0 | 1.20 | 1.64 | 61 |
| 3 | 9.0 | 0 | 1.0 | 1.77 | 6.74 | 53 |
| 4 | 8.7 | 0.45 | 0.95 | 1.08 | 1.24 | 51 |

TABLE 3.2

MP Ursodiol data (10% w/w Ursodiol, 5.5% Mannitol)
Particle size at 4 C.

| Sample | w/w % Lipoid E80 | w/w % DPPE | w/w % Tetronic 908 | Initial size (microns) | Final size (microns) | Days |
|---|---|---|---|---|---|---|
| 1 | 2.4 | 0 | 0 | 1.36 | 1.52 | 30 |
| 2 | 1.6 | 0 | 0.8 | 1.15 | 1.20 | 29 |
| 3 | 2.0 | 0.4 | 0 | 1.34 | 1.33 | 27 |
| 4 | 1.41 | 0.28 | 0.72 | 1.06 | 1.13 | 26 |
| 5 | 0 | 0.4 | 2.0 | 1.37 | 1.34 | 13 |

TABLE 3.3

MP Ursodiol data (10% w/w Ursodiol, 5.5% Mannitol)
Particle size at room temperature

| Sample | w/w % Lipoid E80 | w/w % DPPE | w/w % Tetronic 908 | Initial size (microns) | Final size (microns) | Days |
|---|---|---|---|---|---|---|
| 1 | 2.4 | 0 | 0 | 1.36 | 1.51 | 30 |
| 2 | 1.6 | 0 | 0.8 | 1.15 | 1.19 | 29 |
| 3 | 2.0 | 0.4 | 0 | 1.34 | 1.55 | 29 |
| 4 | 1.41 | 0.28 | 0.72 | 1.06 | 1.13 | 26 |
| 5 | 0 | 0.4 | 2.0 | 1.37 | 1.44 | 24 |

TABLE 3.4

MP Ursodiol data (10% w/w Ursodiol, 5.5% Mannitol)
Particle size at 40 C.

| Sample | w/w % Lipoid E80 | w/w % DPPE | w/w % Tetronic 908 | Initial size (microns) | Final size (microns) | Days |
|---|---|---|---|---|---|---|
| 1 | 2.4 | 0 | 0 | 1.36 | 1.51 | 30 |
| 2 | 1.6 | 0 | 0.8 | 1.15 | 1.23 | 29 |
| 3 | 2.0 | 0.4 | 0 | 1.34 | 1.35 | 27 |
| 4 | 1.41 | 0.28 | 0.72 | 1.06 | 1.12 | 26 |
| 5 | 0 | 0.4 | 2.0 | 1.37 | 1.35 | 20 |

TABLE 3.5

MP Ursodiol data (10% w/w Ursodiol, 5.5% Mannitol)
Shaking stability data at room temperature

| Sample | w/w % Lipoid E80 | w/w % DMPG | w/w % Tetronic 908 | Initial size (microns) | Final size (microns) | Days |
|---|---|---|---|---|---|---|
| 1 | 2.4 | 0 | 0 | 1.36 | — | — |
| 2 | 1.6 | 0 | 0.8 | 1.15 | 1.17 | 15 |
| 3 | 2.0 | 0.4 | 0 | 1.34 | 1.36 | 7 |
| 4 | 1.41 | 0.28 | 0.72 | 1.06 | 1.09 | 7 |
| 5 | 0 | 0.4 | 2.0 | 1.37 | 1.37 | 7 |

TABLE 3.6

MP Ursodiol data (10% w/w Ursodiol, 5.5% Mannitol)
Thermal cycling stability data (after 3 cycles)

| Sample | w/w % Lipoid E80 | w/w % DMPG | w/w % Tetronic 908 | Initial size (microns) | Final size (microns) |
|---|---|---|---|---|---|
| 1 | 2.4 | 0 | 0 | 1.36 | — |
| 2 | 1.6 | 0 | 0.8 | 1.15 | 1.21 |
| 3 | 2.0 | 0.4 | 0 | 1.34 | 1.36 |
| 4 | 1.41 | 0.28 | 0.72 | 1.06 | 1.13 |

TABLE 3.7

MP Fenofibrate data (10% w/w Fenofibrate, 5.5% Mannitol)
Particle size at 4 C.

| Sample | w/w % Lipoid E80 | w/w % DMPG | w/w % Poloxamer 407 | Initial size (microns) | Final size (microns) | Days |
|---|---|---|---|---|---|---|
| 1 | 4.0 | 0 | 0 | 0.95 | 3.59 | 30 |
| 2 | 3.0 | 0 | 1.0 | 0.86 | 1.10 | 33 |

TABLE 3.7-continued

MP Fenofibrate data (10% w/w Fenofibrate, 5.5% Mannitol)
Particle size at 4 C.

| Sample | w/w % Lipoid E80 | w/w % DMPG | w/w % Poloxamer 407 | Initial size (microns) | Final size (microns) | Days |
|---|---|---|---|---|---|---|
| 3 | 3.6 | 0.4 | 0 | 0.85 | 2.91 | 33 |
| 4 | 2.77 | 0.31 | 0.92 | 0.82 | 1.17 | 32 |

TABLE 3.8

MP Fenofibrate data (10% w/w Fenofibrate, 5.5% Mannitol)
Particle size at 25 C.

| Sample | w/w % Lipoid E80 | w/w % DMPG | w/w % Poloxamer 407 | Initial size (microns) | Final size (microns) | Days |
|---|---|---|---|---|---|---|
| 1 | 4.0 | 0 | 0 | 0.95 | 6.47 | 30 |
| 2 | 3.0 | 0 | 1.0 | 0.86 | 1.32 | 29 |
| 3 | 3.6 | 0.4 | 0 | 0.85 | 8.10 | 29 |
| 4 | 2.77 | 0.31 | 0.92 | 0.82 | 1.39 | 28 |

TABLE 3.9

MP Fenofibrate data (10% w/w Fenofibrate, 5.5% Mannitol)
Shaking stability data

| Sample | w/w % Lipoid E80 | w/w % DMPG | w/w % Poloxamer 407 | Initial size (microns) | Final size (microns) | Days |
|---|---|---|---|---|---|---|
| 1 | 4.0 | 0 | 0 | 0.95 | 3.53 | 8 |
| 2 | 3.0 | 0 | 1.0 | 0.86 | 1.27 | 7 |
| 3 | 3.6 | 0.4 | 0 | 0.85 | 2.86 | 7 |
| 4 | 2.77 | 0.31 | 0.92 | 0.82 | 1.32 | 7 |

TABLE 3.10

MP Fenofibrate data (10% w/w Fenofibrate, 5.5% Mannitol)
Thermal cycling stability data

| Sample | w/w % Lipoid E80 | w/w % DMPG | w/w % Poloxamer 407 | Initial size (microns) | Final size (microns) | # cycles |
|---|---|---|---|---|---|---|
| 1 | 4.0 | 0 | 0 | 0.95 | 3.59 | 3 |
| 2 | 3.0 | 0 | 1.0 | 0.86 | 2.26 | 3 |
| 3 | 3.6 | 0.4 | 0 | 0.85 | 8.61 | 3 |
| 4 | 2.77 | 0.31 | 0.92 | 0.82 | 2.54 | 3 |

The sample (example 4) prepared with a combination of charged and steric surface modifiers showed good stability under all conditions.

The presence of a charged and steric surface modifiers during the formation of micron to sub-micron sized phospholipid coated microparticles provides for the high rate of production of minimally sized particles. Also, the combination of effect of steric and electrostatic stabilizers provides best stability and prevents or minimizes particle growth due to both Ostwald ripening and particle aggregation. Further, charged surface modifiers appear possibly to contribute mostly to particle size reduction whereas steric modifiers contribute mostly to stability.

The above data demonstrate the presence of a charged and steric surface modifiers during the formation of micron to sub-micron sized phospholipid coated microparticles provides for a high rate of production of minimally sized particles.

The following materials were used in the above examples:

TABLE 1

Surface Modifiers

| Full Name | Abbreviation | Class of surface modifier | Type of stabilization |
|---|---|---|---|
| Lipoid E-80 | LipE80 | Phospholipid | |
| 1,2-Dimyristoyl-sn-Glycero-3-[Phospho-rac-(1-glycerol)] (Sodium Salt) | DMPG | Charged | Electrostatic |
| 1,2-Dipalmitoyl-sn-Glycero-3-Phosphoethanolamine | DPPE | Charged | Electrostatic |
| Pluronic F127 (also known as Poloxamer 407) | PF127 | Block Copolymer | Steric |
| Tetronic 908 | T908 | Block Copolymer | Steric |
| Pluronic F68 (also known as Poloxomer 188) | PF68 | Block copolymer | Steric |

TABLE 2

List of Suppliers

| Name | Supplier | Location |
|---|---|---|
| Cyclosporine | North China Pharmaceutical Company | China |
| Ursodiol | Tokyo Tanabee | Tokyo, Japan |
| Fenofibrate | Laboratorio Chimico Internazionale s.p.a. | Milan, Italy |
| Lipoid E-80 | Lipoid GMBH | Ludwigshafen, Germany |
| DMPG, DPPE | Avanti Polar Lipids | Alabaster, Alabama, U.S.A. |
| Tetronic and Pluronic Block Polymers | BASF | Mount Olive, New Jersey, U.S.A. |

What is claimed is:

1. A method of increasing the rate of microparticle formation in a pharmaceutical composition mixed with water comprising particles of a water-insoluble or poorly soluble drug having phospholipid coated surfaces, said method comprising homogenizing or microfluidizing said drug to produce coated drug microparticles in the presence of natural phospholipid, a highly purified charged phospholipid surface modifier and a block copolymer of ethylene oxide and propylene oxide, wherein the charged phospholipid surface modifier provides electrostatic stabilization and the block copolymer of ethylene oxide and propylene oxide provides steric stabilization against Ostwald ripening and particle aggregation resulting in particles having a volume weighted mean particle size diameter of about 0.05 to about 10 microns, and wherein in the presence of said natural phospholipid, a combination effect of said steric stabilizing block copolymer of ethylene oxide and propylene oxide and said charged phospholipid surface modifier stabilizers gives a smaller terminal particle size than by using either alone, the total weight percent of surface modifiers kept constant.

2. A method of increasing the rate of particle formation in a pharmaceutical composition mixed with water comprising particles of a water-insoluble or poorly soluble drug, comprising homogenizing or microfluidizing the drug in the presence of a mixture of 0.01% to 50% wt of naturally occurring phospholipid, 0.01 to 5.0% wt of highly purified charged phospholipid surface modifier and 0.01 to 20% wt of a steric stabilizing block copolymer of ethylene oxide and propylene oxide, wherein the charged phospholipid surface modifier provides electrostatic stabilization and the block copolymer of ethylene oxide and propylene oxide provides steric stabilization against Ostwald ripening and particle aggregation resulting in particles having volume weighted mean particle size diameters of about 0.05 microns to about 10 microns, and wherein in the presence of said natural phospholipid, a combination effect of said steric stabilizing block copolymer of ethylene oxide and propylene oxide and said charged phospholipid surface modifier stabilizers gives a smaller terminal particle size than by using either alone, the total weight percent of surface modifiers kept constant.

* * * * *